United States Patent [19]

De Pasquale et al.

[11] 3,933,831

[45] Jan. 20, 1976

[54] PERFLUORINATED TERTIARY AMINES

[75] Inventors: Ralph J. De Pasquale; Keith B. Baucom, both of Gainesville, Fla.

[73] Assignee: PCR, Inc., Gainesville, Fla.

[22] Filed: Nov. 7, 1973

[21] Appl. No.: 413,440

[52] U.S. Cl. .......................... 260/293.51; 252/63.7
[51] Int. Cl.$^2$ ..................................... C07D 211/00
[58] Field of Search .................. 260/293.51, 293.72

[56] References Cited
UNITED STATES PATENTS
2,490,098   12/1949   Simons ........................... 260/293

OTHER PUBLICATIONS
Mazalov et al., Zh. Obshch. Khim., 35(3), 485–489, (1965), C.A.63:2628b.
Sokolov et al., Zh. Obshch. Khim., 36(9), 1613–1618, (1966), C.A.66:54884x.
Plashkin et al., Zh. Obshch. Khim., 36(9), 1708–1709, (1966), C.A.66:55354m.
Ryabinin et al., Zh. Obshch. Khim., 37(6), 1229–1232, (1967), C.A.68:29493c.
Banks et al., J. Chem. Soc., C 1968(21), 2608–2612, C.A.70:3780k.

*Primary Examiner*—G. Thomas Todd
*Attorney, Agent, or Firm*—Cushman, Darby & Cushman

[57] ABSTRACT

Thermally and oxidatively stable perfluorinated tertiary amines of the formula:

$$R^1{}_f N - R^1{}_f$$

are disclosed, as well as the process for making these and other compounds. The carbonyl group of imides or amides is reduced with $SF_4$ using HF as the reaction solvent at a reaction temperature of 25°–300°C. Cyclic imides can be used as starting compounds, and tertiary amines containing unsaturated moieties can be produced.

The perfluorinated tertiary amines have various uses in view of their high degree of thermal and oxidative stability, including uses as hydraulic fluids or transformer dielectric fluids.

2 Claims, No Drawings

PERFLUORINATED TERTIARY AMINES

BACKGROUND OF THE INVENTION

The prior art has prepared perfluorinated tertiary amines by electrolysis (note, e.g. U.S. Pat. No. 2,616,927). Only saturated perfluorinated tertiary amines can be prepared by such electrolytic route. Furthermore, the saturated perfluorinated tertiary amines prepared by the electrolytic method contain isomers, as during electrolysis normal chains partially isomerize to branched chains. Thus, it is difficult to obtain pure components using the electrolytic method without also utilizing tedious purification processes.

U.S. Pat. No. 2,859,245 discloses the preparation of organic fluorine compounds by reacting certain organic compounds, including carboxylic acid amides, with $SF_4$, preferably with the use of hydrogen fluoride as catalyst. Example 18 involves the reduction of N,N-dimethylbenzamide to α-α-difluorobenzyldimethylamine in low yield. In *J. Am. Chem. Sec.*, 82 543–551, 548 (1960), the patentee and others state that the reaction could not be reproduced consistently, with the suggestion that the reaction of an amide with $SF_4$ to cleave the carbonyl-nitrogen bond is catalyzed by trace amounts of HF. The prior art has prepared perfluorinated tertiary amines using other processes, with, e.g. $(R_f)_2$ NF used as an intermediate. Note, e.g. Banks et al., J. C. S. Perkin I, 1098 (1972). These routes do not appear to be feasible for commercial production, due to low yields and broad distributions of products obtained.

Other papers of interest as background to the present invention are *J. Am. Chem. Soc.*, 87, 4338 (1965); *J. Am. Chem. Soc.*, 80, 3604 (1958); *J. Am. Chem. Soc.*, 84, 2105 (1962); and *J. Chem. Sec.* (C), 2920 (1971).

SUMMARY OF THE INVENTION

A process for producing perfluorinated tertiary amines is disclosed, wherein the carbonyl group or groups of an imide or amide is reduced with $SF_4$ at a reaction temperature of 25°–300°C using HF as the reaction solvent. Certain perfluorinated tertiary amines produced by the process of this invention are novel, and these amines are of the formula

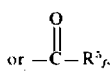

DESCRIPTION OF THE INVENTION

The present invention is directed to a process for preparing perfluorinated tertiary amines, and to certain novel perfluorinated tertiary amines.

The process involves reducing a carbonyl group of an N-substituted imide or an N,N-disubstituted amide with $SF_4$ using HF as the reaction solvent, at a reaction temperature of 25° to 300°C. The reaction proceeds rapidly and essentially complete conversion is achieved within a relatively short period of time at relatively low reaction temperatures. Preferably the process reduces an imide, most preferably a cyclic imide, as the process does not seem to work quite as well with non-cyclic imides.

The imides and amides which are to be reduced have the structural formula:

wherein $n_2$ is 1 or 2, $R^6_f$ is $R^1_f$

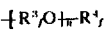

or $-C-R^5_f$.

wherein $R^1_f$ is
a. $R^5_f$, wherein $R^5_f$ is
  I. a perfluorinated radical of 1–12 carbon atoms selected from the group consisting of alkyl, alkaryl, aralkyl and aryl or
  II. a perfluorinated cycloalkyl radical of 4–12 carbon atoms
b. or $R^9_f$, wherein $R^9_f$ is an alkylene oxide radical of the formula:

$$-(R^3_fO)_n-R^4_f$$

wherein
$R^3_f$ is a perfluorinated alkylene radical of 1–3 carbon atoms and $R^4_f$ is a perfluorinated alkyl radical of 1–12 carbon atoms, wherein the total number of carbon atoms in all of the $R^3_f$ groups and the $R^4_f$ group is 2–150, and each A is independently $R^6_f$, provided, however, that if each A is $R^6_f$, at least one but not three of the $R^6_f$ groups is

or both A's, taken together with the nitrogen atom, are
a. a cyclic perfluorinated ring of 2–20 carbon atoms, provided, however, that $R^6_f$ is then

b. a cyclic perfluorinated ring of 4–20 carbon atoms wherein at least one α-carbon atom, relative to the nitrogen atom, carries an oxo substituent,
c. or an isocyanurate ring wherein each ring nitrogen atom carries a $R^1_f$ substituent.

These imides and amides are readily reduced by at least a stoichiometric amount of sulfur tetrafluoride, and preferably about 10–20 moles of sulfur tetrafluoride per mole equivalent of carbonyl groups, although there is no real upper limit on the amount of sulfur tetrafluoride which can be used. The reaction is conducted in anhydrous HF as the reaction solvent. Enough HF must be used to dissolve the reactants, and substantial excesses of HF can be used if desired. Generally, however, there is no advantage to using more than about 90 weight percent, based on the weight of amide or imide compound, of HF in the reaction mixture, and normally the amount of HF will be from about 50 to 90 weight percent in the reaction mixture, based on the weight of amide or imide compound. It is, however, critical that the amount of hydrogen fluoride used is a solvent amount — that is, enough to dissolve the reactants. For instance, if only catalytic amounts of HF are used, as contemplated by U.S. Pat. No. 2,859,245 discussed hereinabove, the reaction will proceed much slower with lower yields and/or conversions. Thus, the unexpectedly improved results obtained by the process of the present invention are directly related to using solvent amounts of hydrogen fluoride. The process reduces the carbonyl group of the imide or the amide, generally substantially without cleavage of the carbonyl carbon-nitrogen bond.

The reaction may be conducted at subatmospheric, atmospheric or superatmospheric pressures as desired. The reaction temperature will generally be within the range of about 0° to 300°C, preferably about 80° to 150°C. Normally the reaction is complete after 12 hours, but at low reaction temperatures it may be desirable to use greater reaction times to insure substantially complete conversion.

The perfluorinated tertiary amine products produced by the process of the present invention have the general formula:

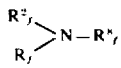

wherein $R_f$ and $R^2_f$ are independently
 a. perfluorinated radicals of 1–13 carbon atoms selected from the group consisting of alkyl and aralkyl,
 b. perfluorinated cycloalkyl radicals of 4–12 carbon atoms,
 c. alkylene oxide radicals of the formula

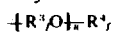

wherein $R^3_f$ is a perfluorinated alkylene radical of 1–3 carbon atoms and $R^4_f$ is a perfluorinated alkyl radical of 1–12 carbon atoms, wherein the total number of carbon atoms in all of the $R^3_f$ groups and the $R^4_f$ group is 2–150,
 d. or together $R_f$ and $R^2_f$, with the nitrogen atom, are a cyclic perfluorinated ring of 2–20 carbon atoms or a perfluorinated hexahydro-s-triazine ring wherein each ring nitrogen atom carries a $R^5_f$ or $R^9_f$ substituent and $R^8_f$ is
 a. $R^5_f$ wherein $R^5_f$ is a perfluorinated radical of 1–12 carbon atoms selected from the group consisting of alkyl, alkaryl, aralkyl and aryl or a perfluorinated cycloalkyl radical of 4–12 carbon atoms,
 b. a radical of the formula:
 $-CF_2 - R^3_f$.
 c. or an alkylene oxide radical of the formula $+R^3_fO+_{n_3}R^4_f$ wherein $R^3_f$ is a perfluorinated alkylene radical of 1–3 carbon atoms and $R^4_f$ is a perfluorinated alkyl radical of 1–12 carbon atoms, wherein the total number of carbon atoms in all of the $R^3_f$ groups and the $R^4_f$ group is 2–150.

Compounds of the formula

wherein $R_f^7$ is $C_n F_{2n}$ or, together with the nitrogen atom, forms a perfluorinated hexahydro-s-triazine ring wherein each ring nitrogen atom carries an $R^5_f$ or $R^9_f$ substituent, $R^8_f$ is
 a. $R^5_f$ wherein $R^5_f$ is a perfluorinated radical of 1–12 carbon atoms selected from the group consisting of alkyl, alkaryl, aralkyl and aryl or a perfluorinated cycloalkyl radical of 4–12 carbon atoms,
 b. a radical of the formula:

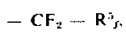

c. or an alkylene oxide radical of the formula

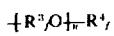

wherein $R^3_f$ is a perfluorinated alkylene radical of 1–3 carbon atoms and $R^4_f$ is a perfluorinated alkyl radical of 1–12 carbon atoms, wherein the total number of carbon atoms in all of the $R^3_f$ groups and the $R^4_f$ group is 2–150 and $n_3$ is 2 to 20,
are believed to be particularly novel. These compounds are readily produced from the corresponding cyclic amides or imides.

Cyclic imides may be readily prepared by the condensation reaction of an isocyanate and an anhydride, according to the reaction equation:

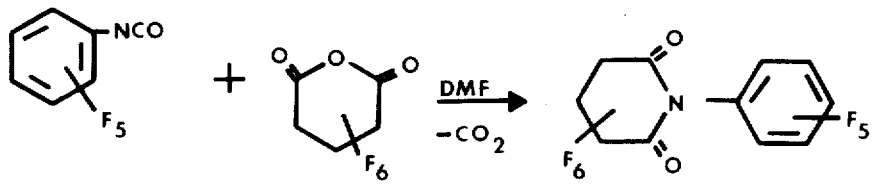

The reaction is conducted in an inert solvent such as DMF and proceeds readily at reaction temperatures of 0° to 150°C. For instance, perfluoro (N-phenylglutarimide) may be readily produced from perfluoroglutaric anhydride and pentafluorophenyl isocyanate in DMF at a temperature of 125°C. It is also possible to prepare polyamines or imines by the condensation of diisocyanates and dianhydrides. The resulting polyamides or polyimides may be reduced with $SF_4$, as described hereinabove, to produce perfluorinated tertiary polyamines.

The polyimides could, for instance, be prepared by the following reaction sequence:

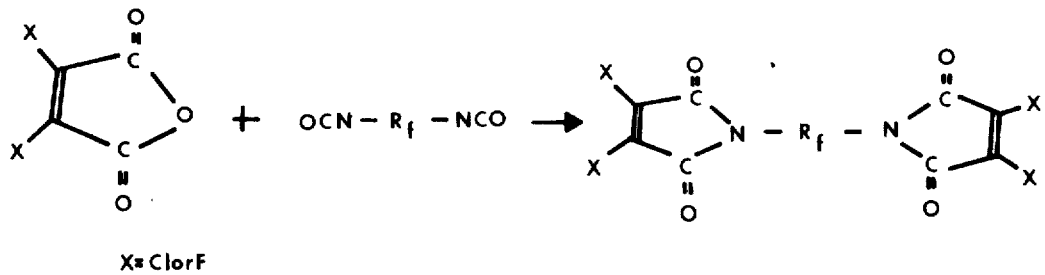

X = Cl or F wherein $R^3_f$ is a perfluorinated alkylene radical of 1–3 carbon atoms and $R^4_f$ is a perfluorinated alkyl The reaction product of Step 1 above can then be subjected to the following step to reduce the carbonyl groups thereof, using SF₄ and HF solvent, according to the process of the present invention:

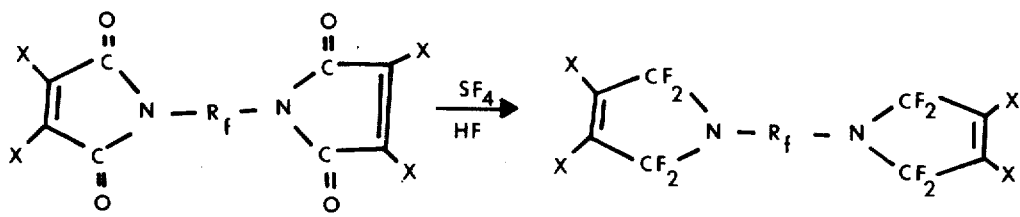

The product of Step 2 may be oxidized using ultraviolet irradiation, according to the following reaction sequence:

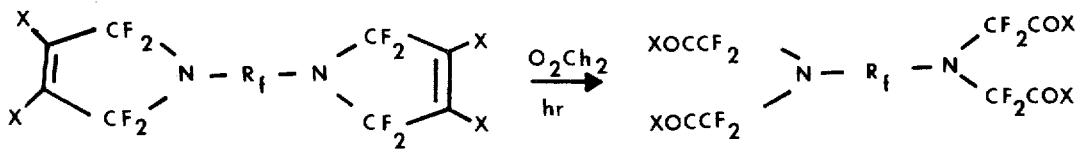

The product of the Step 3 reaction can be cyclicized according to the following reaction sequence:

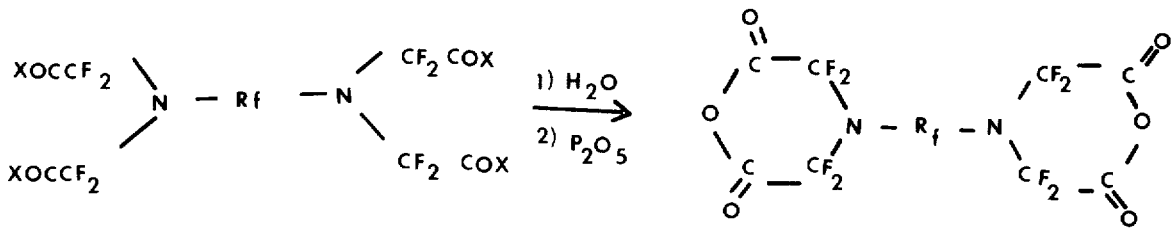

The product of Step 4 can then be reacted with a diisocyanate, which can be the same or different from the first diisocyanate, according to the reaction sequence:

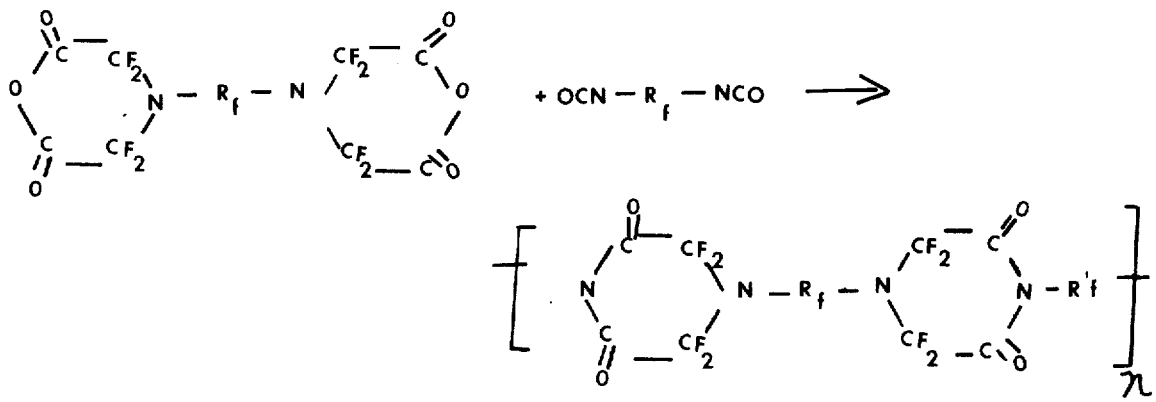

The above polymer can be further fluorinated, using additional amounts of SF₄ with HF solvent, according to the process of the present invention, to convert the imide linkages to tertiary amines according to the following sequence:

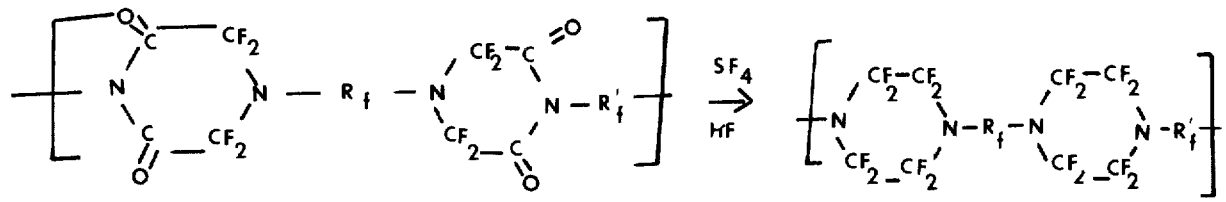

The perfluorinated tertiary amines prepared by the process of the present invention may contain unsaturated moieties, such as perfluorinated phenyl substituents, which is a distinct advantage of the process of the present invention over the electrolytic processes. Furthermore, no isomerization reactions are encountered in the process of the present invention so that it is possible to obtain pure components without tedious purification procedures. Thus, the process of the present invention appears to have a much broader range of applicability than the electrolytic process.

The starting compounds containing groups of the formula $+R^3{}_fO]_\pi R^4{}_f$ may be prepared by various conventional procedures.

For instance, perfluorinated amides may be prepared from the corresponding perfluorinated acid chlorides or fluorides, by the following reaction:

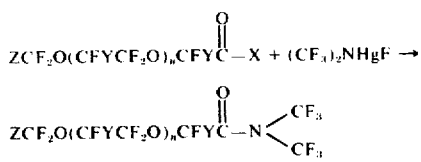

$X = F, Cl$
$Y = F, CF_3$
$Z = CF_3, C_2F_5$

The acid fluoride starting compounds may be prepared using the procedure described in E. P. Moore, A. S. Milian, and H. S. Eleuterio, U.S. Pat. No. 3,250,808(1966), and J. L. Warnell, U.S. Pat. No. 3,125,599(1964), the disclosures of which are hereby incorporated by reference. The corresponding acid chloride compounds can be prepared by hydrolyzing the acid fluorides to the acid, and then converting the acid to the acid chloride using $SOCl_2$.

Another class of compounds containing the perfluorinated ether groups could be prepared using the general procedure described in R. E. Banks, M. G. Barlow, R. N. Haszeldine, and M. K. McCreath, J. Chem. Soc. (C), 1350(1966), according to the following reaction sequence:

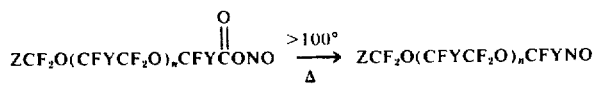

The nitroso compound can be converted into the corresponding aza olefin by the procedure similar to that of A. P. Stefani, J. R. Lacher, and J. D. Park, J. Poly. Sci., 62, 211(1962) using the following reaction sequence:

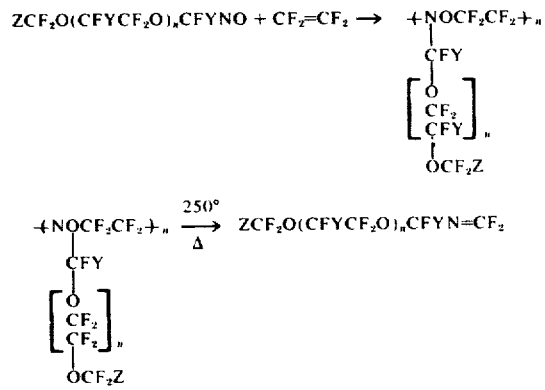

The aza olefin can be converted by reaction with mercuric fluoride according to the following reaction:

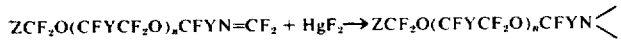

finally, reaction of the compound obtained above with a perfluorinated acid halide proceeds as follows:

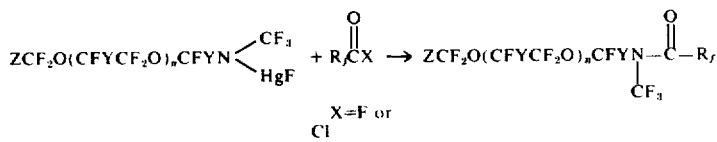

The products produced by the process of the present invention have various uses, due to their high degree of thermal and oxidative stability. The products are normally fluids at ambient conditions, and are useful as hydraulic fluids or dielectric fluids for transformers. Other uses for some of the products are disclosed in U.S. Pat. No. 2,616,927, the disclosure of which is hereby incorporated by reference.

It will be appreciated from the above description that the process of the present invention involves the reduction of 1 or 2 but not 3 imide or amide carbonyl groups attached to a nitrogen atom. More than 2 carbonyl groups in a given compound may be reduced, e.g. in the case of an isocyanurate compound, but in such instances the 3 or more carbonyl groups which are to be reduced are not attached to the same nitrogen atom.

A wide variety of imides or amides of the aforementioned formula $$A_{n_2}N(R^5_f)_{3-n_2}$$

may be reduced by the process of the present invention. Among suitable substituents on the nitrogen atom may be compounds wherein $R^5_f$ is methyl, ethyl, propyl, butyl, octyl, dodecyl, benzyl, phenethyl, naphthyl, phenyl, tolyl, xylyl, methylbenzyl, cycloheptyl, cyclohexyl, cyclopentyl, methoxymethyl, and methoxybutyl. Such compounds include perfluoro(N-methyl-N-propyl octanamide), perfluoro (N-ethoxy methyl-N-methyl acrylamide) perfluoro (N-acetyl pyrrolidine), perfluoro (N-butyryl aziridine), perfluoro (N,N-dihexyl formamide), perfluoro (N-phenyl glutarimide), perfluoro (N-methyl glutarimide), perfluoro(N-octyl glutarimide), perfluoro (N-benzyl succinimide), perfluoro (N-pentyl succinimide), perfluoro (N-butyl adipimide) and perfluoro (N-tolyl adipimide).

EXAMPLES OF THE INVENTION

EXAMPLE 1

A. Preparation of Perfluoro(N-phenylglutarimide)

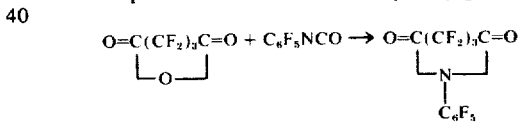

Perfluoroglutaric anhydride (21.2 g, 0.0955 mole), pentafluorophenyl isocyanate (20.0 g, 0.0955 mole) and DMF (0.2 ml) were stirred together at 25°. No gas was evolved. The mixture was heated to reflux and stirred for 15 minutes; still no gas was evolved. Then 5 ml of DMF was added, whereupon gas evolved at a slow but steady rate. The reaction was heated (bath temp. 125°) with stirring overnight. In the morning, gas was no longer evolving. The reaction mixture was dark in color and on cooling solidified. The contents were sublimed at 0.1 mm (50° bath temperature) affording the corresponding imide (30.0 g, theory 37.0 g, 81% yield). This material had a m.p. 70°–72°C. Recrystallization from hexane (25 g imide/100 g hexane) afforded an analytical sample, mp 73°C.

Anal. Calcd. $C_{11}F_{11}NO_2$: C, 34.1; N, 3.62. Found: C, 34.25; N, 3.81.

The $^{19}$F-NMR spectrum showed absorptions (relative to $CF_3CO_2H$) at 42.8 ($CF_2CO$), 58.6 ($CF_2$), 64.9 (aromatic o-fluorine), 68.8 (aromatic p-fluorine), and 80.9 (aromatic m-fluorine) PPM.

B. Preparation of Perfluoro(N-phenylpiperidine)

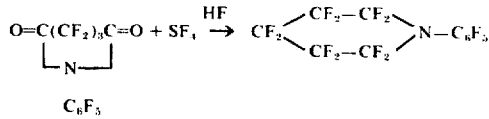

Perfluoro (N-phenylglutarimide) (10.0 g, 0.0266 mole), HF (25 ml), and $SF_4$ (32.6 g, 0.302 mole) were charged in a 300 ml stainless steel autoclave and heated with rocking at 125° for 24 hours. The contents of the autoclave were cooled and vented to remove the $HF/SF_4/SOF_2$ mixture, dissolved in 50 ml of Freon 113, and transferred to a flask containing NaF to remove residual HF. The solution was decanted and distilled, the fraction having B.P. 93°–95°C/40 mm was collected (9.5 g, 86% of theoretical yield) and identified as perfluoro(N-phenylpiperidine).

Anal. Calcd. for $C_{11}F_{15}N$: C, 30.6%; N, 3.24%. Found: C, 30.8%; N, 3.47%.

The mass spectrum showed M at 431 and M-19 at 412 while the $^{19}$F NMR spectrum (relative to $CF_3CO_2H$) showed absorptions at 15.6 ($NCF_2$), 55.8 ($NCF_2\underline{CF_2}$), 56.3 ($NCF_2CF_2\underline{CF_2}$), 65.0 (O-aromatic), 73.0 (p-aromatic) and 85.7 (m-aromatic) PPM.

EXAMPLE 2

A. Preparation of Perfluoro(N,N-dimethyl octanamide)

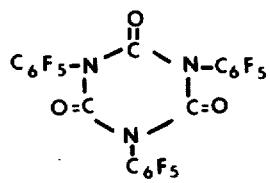

Bis (bis-trifluoromethylamino)mercury (which can be prepared by the method of Young et al., *J. Am. Chem. Soc.*, 80, 3604(1958), the disclosure of which is hereby incorporated by reference)(8.7 g, 0.0172 mole) was frozen at −183°C. Then perfluorooctanoyl chloride (14.9 g, 0.0344 mole) was added rapidly under nitrogen. The mixture was allowed to warm to 25° and maintained at that temperature for 18 hr. At that time the white precipitate that had formed was pressure filtered, washed with Freon-113 (3 × 5 ml), and the resulting solution was distilled. Material of BP 52°–55°/12 mm was collected and identified as perfluoro(N,N-dimethyloctanamide) (11.4 g, 61% yield).

Anal. Calcd. for $C_{10}F_{21}NO$: C, 21.8; N, 2.6. Found: C, 21.6; N, 2.8.

The infrared spectrum showed a carbonyl group at 5.55μ while the $^{19}$F-NMR spectrum (relative to $CF_3CO_2H$) showed absorptions at −22.1 ($NCF_3$), 4.1 ($CF_3$), 38.3 ($CF_2CO$), 43.1 ($CF_2$), 44.7 ($CF_2$) and 48.9 ($CF_2$) PPM.

B. Preparation of Perfluoro(octyl dimethylamine)

Perfluoro(N,N-dimethyl octanamide) (8.7 g, 0.016 mole) HF (40 ml), and $SF_4$ (23.8 g, 0.220 mole) were charged to a 300 ml stainless steel autoclave and heated with rocking at 150°C for 18 hours. The vessel was allowed to cool and vented at 25°C. The contents of the autoclave were dissolved in Freon 113 (50 ml) and then stored over NaF. Decantation followed by distillation afforded perfluoro(octyl dimethylamine), BP 64°–65°C/22 mm (7.1 g, 78% yield).

Anal. Calcd. for $C_{10}F_{23}N$: C, 21.0; N, 2.5. Found: C, 20.7; N, 2.6.

The $^{19}$F-NMR spectrum displayed resonances at −24 ($NCF_3$), 5.0 ($CF_3$), 13.5 ($NCF_2$), 44.9 ($CF_2$) and 49.5 ($CF_3\underline{CF_2}$) PPM relative to $CF_3CO_2H$.

EXAMPLE 3

A. Preparation of Tris-Pentafluorophenyl Isocyanurate

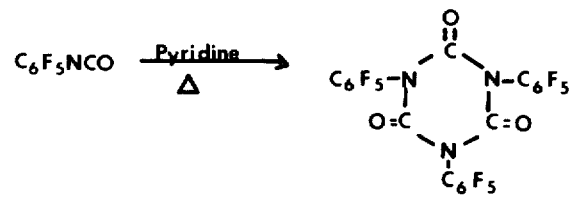

Pentafluorophenyl isocyanate (5.0 g, 0.024 mole) and pyridine (1 ml) were heated at 110°C for 1 hour. The volatiles were removed from the dark resulting mixture in vacuo; the residue was sublimed at 120°/< 1 mm affording a white solid of mp 169°–170°C.

Anal. Calcd for $C_{21}F_{15}N_3O_3$: C, 40.0; N, 6.7. Found: C, 40.0; N, 6.96.

The infrared spectrum (nujol mull) showed a carbonyl band at 5.72μ and C=C aromatic band at 6.6μ.

B. Preparation of Perfluoro (N,N,N-triphenylhexahydro-s-triazine)

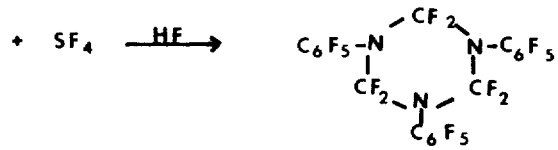

Tris-pentafluorophenyl isocyanaurate (1.0 g, 1.6 mmoles), HF (10 ml), and $SF_4$ (20.2 g, 0.188 mole) were charged in a 100-ml stainless steel autoclave and heated with rocking for 48 hours at 250°C. The autoclave was allowed to cool, then vented at atomspheric pressure. There was obtained a solid material (1.0 g, mp 108°–140°C) which on analysis by GLC revealed its composition as starting material (90%) and another product with slightly less retention time (10%). The latter product was identified as perfluoro(N,N,N-triphenylhexahydro-s-triazine) by NMR, mass spectral, and infrared analysis.

What is claimed is:

1. Perfluorinated tertiary amine of the formula

wherein $R^7_f$ a. is — $C_{n_3}F_{2n_3}$, wherein $n_3$ is 2–20, and $R^8_f$ is a perfluorinated aryl group, wherein any substituents on the aryl ring are perfluorinated alkyl substituents, wherein $R^8_f$ contains about 6–12 carbon atoms.

2. Perfluoro(N-phenylpiperidine).

* * * * *